(12) United States Patent
Fukao et al.

(10) Patent No.: US 8,003,825 B2
(45) Date of Patent: Aug. 23, 2011

(54) PROCESS FOR PRODUCING CYCLOALKANONE OXIMES

(75) Inventors: Masami Fukao, Ritto (JP); Miyuki Oikawa, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/408,061

(22) Filed: Apr. 21, 2006

(65) Prior Publication Data

US 2006/0252962 A1    Nov. 9, 2006

(30) Foreign Application Priority Data

Apr. 25, 2005   (JP) .................. 2005-126117

(51) Int. Cl.
*C07C 259/00* (2006.01)
(52) U.S. Cl. ........ 564/267; 540/535
(58) Field of Classification Search ........ 564/267; 540/535; 514/320
See application file for complete search history.

(56) References Cited

U.S. PATENT DOCUMENTS

| 4,410,501 | A |   | 10/1983 | Taramasso et al. |
| 4,745,221 | A |   | 5/1988  | Roffia et al. |
| 4,794,198 | A | * | 12/1988 | Roffia et al. ........ 564/267 |
| 5,227,525 | A | * | 7/1993  | Tonti et al. ........ 564/267 |
| 5,312,987 | A |   | 5/1994  | Mantegazza et al. |
| 5,451,701 | A |   | 9/1995  | Zajacak et al. |
| 6,828,459 | B2 |  | 12/2004 | Oikawa et al. |
| 2003/0100795 | A1 | | 5/2003 | Herwig et al. |
| 2004/0204609 | A1 | | 10/2004 | Oikawa et al. |

FOREIGN PATENT DOCUMENTS

| EP | 0496385 A1 | 7/1992 |
| EP | 0564040 A2 | 10/1993 |
| JP | 63-130575  | 6/1988 |
| JP | 2003-183237 | 7/2003 |

OTHER PUBLICATIONS

Roffia et al., Studies in Surface Science and Catalysis, vol. 55, pp. 43-52, (1990).
Japanese Office Action dated Jan. 26, 2010 issued in corresponding Japanese Patent Application No. 2005-126117.

* cited by examiner

*Primary Examiner* — Sudhakar Katakam
(74) *Attorney, Agent, or Firm* — Birch, Stewart, Kolasch & Birch, LLP

(57) ABSTRACT

The present invention provides a process for producing a cycloalkanone oxime by conducting a continuous ammoximation reaction in the presence of a titanosilicate catalyst with supplying a cycloalkanone, hydrogen peroxide, ammonia and an organic solvent into the reaction system, wherein the reaction temperature is from 90° C. to 120° C. and the supplying amount of the organic solvent is not more than 2 times by weight of that of the cycloalkanone.

5 Claims, No Drawings

PROCESS FOR PRODUCING CYCLOALKANONE OXIMES

BACKGROUND OF THE INVENTION

1. Field of the Invention

The present invention relates to a process for producing a cycloalkanone oxime by the ammoximation reaction of a cycloalkanone. Cycloalkanone oximes are useful as raw materials for lactams and the like.

2. Description of the Related Art

A process for producing a cycloalkanone oxime includes an ammoximation reaction of a cycloalkanone with hydrogen peroxide and ammonia in the presence of a titanosilicate catalyst (see, for example, U.S. Pat. Nos. 4,745,221, 4,794,198, 5,312,987, 5,227,525, 6,828,459, and U.S. 2004/204609 A). The ammoximation reaction is advantageously carried out in a continuous method in view of productivity or operationality, and usually carried out in an organic solvent as a reaction solvent.

For example, U.S. Pat. No. 4,794,198 discloses a continuous ammoximation reaction of a cyclohexanone using t-butyl alcohol in an amount of from 0.1 to 100 times by mole, preferably from 0.5 to 10 times by mole of the cyclohexanone at from 60° C. to 120° C., and specifically it discloses a reaction using t-butyl alcohol in an amount of 2.1 times by weight of cyclohexanone at 83° C. and a reaction using t-butyl alcohol in an amount of 3.2 or more times by weight of cyclohexanone at 80° C.

U.S. Pat. No. 5,312,987 and U.S. Pat. No. 5,227,525 disclose a continuous ammoximation reaction of a carbonyl compound such as a cycloalkanone using an organic solvent in an amount of from 2.5 to 10 times by weight of the carbonyl compound at from 60° C. to 100° C., preferably at from 70° C. to 90° C., and specifically they disclose a continuous ammoximation reaction of cyclohexanone using t-butyl alcohol in an amount of 2.9 or more times by weight of cyclohexanone at 85° C.

Moreover, U.S. Pat. No. 6,828,459, and U.S. 2004/204609 A disclose a continuous ammoximation reaction of cyclohexanone using an organic solvent at from 50° C. to 100° C., and specifically they disclose a reaction using t-butyl alcohol in an amount of 3.3 times by weight of cyclohexanone at 85° C.

SUMMARY OF THE INVENTION

In the continuous ammoximation reaction of a cycloalkanone as described above, it is advantageous that the amount of the organic solvent used is reduced as much as possible from the viewpoint that an energy cost for recovery or purification of the organic solvent and an equipment cost can be reduced and volumetric efficiency can be improved. However, when the amount of the organic solvent is reduced, an activity of catalyst is apt to be deteriorated resulting in difficult to conduct a long-term operation, so productivity of a cycloalkanone may become insufficient. Thus, the object of the present invention is to provide a process for producing a cycloalkanone oxime by a continuous ammoximation reaction of a cycloalkanone in high yield for a long period of time even when an amount of an organic solvent used is small.

As a result of extensive investigations, the present inventors have found that the above-described object can be achieved by employing an increased reaction temperature, which have been usually considered to be disadvantageous in terms of a catalyst life, and accomplished the present invention. That is, the present invention provides a process for producing a cycloalkanone oxime by conducting a continuous ammoximation reaction in the presence of a titanosilicate catalyst with supplying a cycloalkanone, hydrogen peroxide, ammonia and an organic solvent into the reaction system, wherein the reaction temperature is from 90° C. to 120° C. and the supplying amount of the organic solvent is not more than 2 times by weight of that of the cycloalkanone.

According to the present invention, the continuous ammoximation reaction of a cycloalkanone can produce a cycloalkanone oxime in high yield for a long period of time even when an amount of an organic solvent used is small.

DETAILED DESCRIPTION OF THE PREFERRED EMBODIMENTS

The titanosilicate used as a catalyst in the present invention has titanium, silicon and oxygen as the elements which constitute the molecular skeleton. The molecular skeleton of the titanosilicate may be constituted substantially only by titanium, silicon and oxygen, or may further include other elements. The titanosilicate having the atomic ratio of silicon to titanium being from 10 to 1000 is suitable for use in the present invention, and the shape thereof may be, for example, in the form of fine powder or pellet. The titanosilicate can be produced according to, for example, a method described in JP-A-S56-96720.

By using the titanosilicate described above as a catalyst, the desired cycloalkanone oxime can be produced through the ammoximation reaction of a cycloalkanone with hydrogen peroxide and ammonia in the presence of the catalyst. In the present invention, the ammoximation reaction is conducted continuously with using an organic solvent as a reaction solvent.

The cycloalkanone used in the present invention usually has 5 to 12 carbon atoms. Examples of the cycloalkanone generally include cyclopentanone, cyclohexanone, cyclooctanone and cyclododecanone. The cycloalkanone may be obtained, for example, by oxidation of a cycloalkane, or by hydration and dehydrogenation of a cycloalkene. In addition, as to cyclohexanone, it may be obtained by hydrogenation of phenol.

Hydrogen peroxide is generally produced by so-called anthraquinone process, and is commercially available as an aqueous solution having a concentration of from 10% by weight to 70% by weight, which can be used in the present invention. The amount of hydrogen peroxide to be used is generally from 0.5 to 3 mol, preferably from 0.5 to 1.5 mol, relative to one mol of a cycloalkanone. To the hydrogen peroxide may be added, for example, a small amount of a stabilizing agent including a phosphate such as sodium phosphate, a polyphosphate such as sodium pyrophosphate and sodium tripolyphosphate, pyrophosphoric acid, ascorbic acid, ethylenediaminetetraacetic acid, diethylenetriaminepentaacetic acid and the like, or a derivative thereof.

Ammonia may be used in the form of gas or liquid, or a solution in water or an organic solvent. The amount of ammonia to be used is generally not less than 1 mol, preferably not less than 1.5 mol, relative to one mol of a cycloalkanone.

Examples of the organic solvent include alcohols such as methyl alcohol, ethyl alcohol, n-propyl alcohol, isopropyl alcohol, n-butyl alcohol, S-butyl alcohol, t-butyl alcohol and t-amyl alcohol; aromatic hydrocarbons such as benzene, toluene, xylene and ethylbenzene; and ethers such as tetrahydrofuran, dioxane, diisopropyl ether and t-butyl methyl ether. Two or more of those may be used in combination if neccessary. Among them, since a liquid phase of a reaction mixture is easily kept in uniform state, alcohols having 1 to 6 carbon atoms are preferably used.

An amount of the organic solvent to be used is not more than 2 times by weight, preferably 1.8 times by weight to the cycloalkanone. By reducing an amount of the organic solvent to be used, an energy cost for recovery or purification of the organic solvent and/or an equipment cost can be reduced, and volumetric efficiency can be improved. The reduced organic solvent also can have a problem in productivity, because a catalyst is apt to be deteriorated when the less amount of an organic solvent is used, however, the problem can be settled by increasing a reaction temperature. But, too small amount of the organic solvent is still unfavorable for a catalyst life. Accordingly, the amount of the organic solvent to be used is generally not less than 0.2 times by weight, preferably not less than 0.5 times by weight to the cycloalkanone.

As a reaction solvent, the organic solvent may be used together with water. A mixed solvent of the alcohol described above and water is a preferable example of a reaction solvent. When using water, it is advantageous from the viewpoint of a catalyst life that an amount of water to be used is adjusted so that a water concentration in a liquid phase of a reaction mixture is from 25% by weight to 35% by weight with taking an amount generated by the reaction into consideration.

In the present invention, the continuous ammoximation reaction of a cycloalkanone is conducted with supplying a cycloalkanone, hydrogen peroxide, ammonia and a solvent into the reaction system; practically is conducted in a continuous reactor such as a stirrer-type reactor and loop-type reactor, with supplying a cycloalkanone, hydrogen peroxide, ammonia and a solvent thereinto, to keep a proper amount of the reaction mixture including a titanosilicate catalyst dispersed therein, while simultaneously extracting the resulting reaction mixture by the amount substantially same as supplying amount of these raw materials. The method of supplying the raw materials may include a method where each raw material is supplied separately or together, some of the raw materials are mixed beforehand and the mixture is supplied with other mixture or a raw material, and the like. Upon extracting the resulting reaction mixture, it is favorable that only its liquid phase is extracted through a filter or the like while the catalyst remains in the reactor. The concentration of the catalyst, which depends on the activity thereof, reaction conditions and the like, is generally from 1 g/L to 200 g/L based on the weight per volume of the reaction mixture (the total amount of the catalyst and liquid phase). In addition, in view of suppressing the decrease of catalytic performance of titanosilicate, silicon compounds other than the titanosilicate such as silica, silicate or the like may be used in combination according to the disclosure in JP-A-2004-83560.

The reaction temperature is not less than 90° C. By employing such a higher reaction temperature, the problem in productivity accompanying the reduced amount of organic solvent as described above can be settled, and a cycloalkanone oxime can be produced in high yield for a long period of time. However, too high reaction temperature may easily lead to the thermolysis of hydrogen peroxide, the thermolysis of a hydroxylamine that is an intermediate generated from hydrogen peroxide and ammonia, and the thermolysis of a desired cycloalkanone oxime, and thus lead to the deterioration of a reaction performance. Accordingly, the reaction temperature is not more than 120° C., and preferably not more than 110° C.

The reaction may be conducted at normal atmospheric pressure. In order to increase an amount of ammonia dissolved in the liquid phase of the reaction mixture, the reaction is preferably conducted under pressurized conditions. In this case, the pressure may be adjusted using an inert gas such as nitrogen and helium. The reactor is preferably one lining treated with fluororesin or glass, or made of stainless steel, from the viewpoint of preventing hydrogen peroxide from decomposition.

The post treatment procedure of the resultant reaction mixture is appropriately selected from known methods. For instance, the post treatment procedure can be carried out as described in U.S. Pat. No. 5,227,525: the solvent and any unreacted ammonia remaining are separated and collected as a fraction of distillate by distilling the liquid phase of the reaction mixture, and the bottom product including a cycloalkanone oxime is obtained; thus obtained bottom product is extracted with an organic solvent to obtain an extract of the cycloalkanone oxime. If needed the extract is washed with water, then concentrated, and distilled if needed to obtain a purified cycloalkanone oxime. The solvent and unreacted ammonia collected may be recycled.

EXAMPLES

The present invention is described in more detail by following Examples, which should not be construed as a limitation upon the scope of the present invention.

Reference Example 1

500 mL autoclave, the inner surface of which is lining treated with fluororesin, was used as a reactor. A continuous ammoximation reaction was conducted with supplying cyclohexanone at 12.95 g/h, t-butyl alcohol including 15% by weight of water at 46.04 g/h [wherein, t-butyl alcohol was 39.13 g/h (3.0 times by weight of cyclohexanone)], ammonia at 4.26 g/h, and 60% by weight of hydrogen peroxide in water at 8.60 g/h into the reactor and simultaneously extracting the liquid phase of the reaction mixture through a stainless steal sintered metal filter so that a volume of the reaction mixture in the reactor is kept at about 100 mL under the conditions of a reaction temperature of 85° C. and a reaction pressure of 0.25, MPa. During this period of reaction, 1.0 g of titanosilicate [titanium silicalite (TS-1)] having MFI structure presented in the reaction mixture in the reactor as a catalyst (a supplying rate of the cyclohexanone relative to the catalyst=0.132 mol/h·g-catalyst). At the same time, helium gas was flowed at 1.2 L/h in the gas phase within the reactor and an oxygen concentration in an exhaust gas was monitored as an index of catalyst deterioration. 100 hours after the start of the reaction (the total supplied amount of the cyclohexanone relative to the catalyst=13.2 mol/g-catalyst), since an oxygen concentration in an exhaust gas exceeded 10% by volume, the reaction was terminated.

Comparative Example 1

A continuous ammoximation reaction at 85° C. was conducted similarly as in Reference Example 1, except that supplying rate of cyclohexanone was at 19.56 g/h, that of t-butyl alcohol including 15% by weight of water was at 34.76 g/h [wherein, t-butyl alcohol was 29.55 g/h (1.5 times by weight of cyclohexanone)], that of ammonia was at 6.43 g/h, and that of 60% by weight of hydrogen peroxide in water was at 12.99 g/h, and 1.51 g of the catalyst presented in the reaction mixture in the reactor (a supplying rate of the cyclohexanone relative to the catalyst =0.132 mol/h·g-catalyst). 77 hours after the start of the reaction (the total supplied amount of the cyclohexanone relative to the catalyst=10.2 mol/g-catalyst), since an oxygen concentration in an exhaust gas exceeded 10% by volume, the reaction was terminated.

Example 1

A continuous ammoximation reaction was conducted similarly as in Comparative Example 1, except that a reaction temperature was 90° C. 125 hours after the start of the reaction (the total supplied amount of the cyclohexanone relative to the catalyst=16.2 mol/g-catalyst), since an oxygen concentration in an exhaust gas exceeded 10% by volume, the reaction was terminated.

Example 2

A continuous ammoximation reaction was conducted similarly as in Comparative Example 1, except that a reaction temperature was 95° C. 144 hours after the start of the reaction (the total supplied amount of the cyclohexanone relative to the catalyst=19.0 mol/g-catalyst), since an oxygen concentration in an exhaust gas exceeded 10% by volume, the reaction was terminated.

Example 3

A continuous ammoximation reaction was conducted similarly as in Comparative Example 1, except that a reaction temperature was 105° C. 203 hours after the start of the reaction (the total supplied amount of the cyclohexanone relative to the catalyst=26.8 mol/g-catalyst), since an oxygen concentration in an exhaust gas exceeded 10% by volume, the reaction was terminated.

Example 4

A continuous ammoximation reaction was conducted similarly as in Comparative Example 1, except that a reaction temperature was 115° C. 248 hours after the start of the reaction (the total supplied amount of the cyclohexanone relative to the catalyst=32.7 mol/g-catalyst), since an oxygen concentration in an exhaust gas exceeded 10% by volume, the reaction was terminated.

Example 5

A continuous ammoximation reaction was conducted similarly as in Reference Example 1, except that supplying rate of cyclohexanone was at 18.52 g/h, that of t-butyl alcohol including 15% by weight of water was at 32.92g/h [wherein, t-butyl alcohol was 27.98 g/h (1.5 times by weight of cyclohexanone)], that of ammonia was at 6.10 g/h, and that of 45% by weight of hydrogen peroxide in water was at 16.40 g/h, and 1.43 g of the catalyst presented in the reaction mixture in the reactor (a supplying rate of the cyclohexanone relative to the catalyst=0.132 mol/h·g-catalyst), and a reaction temperature was 95° C. 178 hours after the start of the reaction (the total supplied amount of the cyclohexanone relative to the catalyst=23.5 mol/g-catalyst), since an oxygen concentration in an exhaust gas exceeded 10% by volume, the reaction was terminated.

For each of the above examples, a reaction mixture was analyzed by gas chromatography at a proper time after the reaction started, and a conversion of cyclohexanone, a selectivity to cyclohexanone oxime and a yield of cyclohexanone oxime were determined. Results are listed in Table 1.

TABLE 1

| | Time after the reaction started (h) | | | | | | | |
|---|---|---|---|---|---|---|---|---|
| [Reference Example 1] | | 21 | 41 | 65 | 89 | | | |
| Temperature: 85° C. | Conversion (%) | 98.69 | 98.46 | 98.43 | 98.76 | | | |
| Solvent: 3.0 times | Selectivity (%) | 99.62 | 99.59 | 99.61 | 99.61 | | | |
| (60% $H_2O_2$ was used) | Yield (%) | 98.31 | 98.06 | 98.04 | 98.37 | | | |
| [Comparative Example 1] | Time after the reaction started (h) | 17 | 44 | 68 | | | | |
| Temperature: 85° C. | Conversion (%) | 99.61 | 99.74 | 99.80 | | | | |
| Solvent: 1.5 times | Selectivity (%) | 99.61 | 99.62 | 99.59 | | | | |
| (60% $H_2O_2$ was used) | Yield (%) | 99.22 | 99.36 | 99.40 | | | | |
| [Example 1] | Time after the reaction started (h) | 9 | 36 | 60 | 85 | 110 | | |
| Temperature: 90° C. | Conversion (%) | 99.74 | 99.66 | 99.95 | 99.89 | 99.92 | | |
| Solvent: 1.5 times | Selectivity (%) | 99.62 | 99.58 | 99.54 | 99.53 | 99.47 | | |
| (60% $H_2O_2$ was used) | Yield (%) | 99.36 | 99.24 | 99.48 | 99.42 | 99.39 | | |
| [Example 2] | Time after the reaction started (h) | 32 | 56 | 81 | 106 | 128 | | |
| Temperature: 95° C. | Conversion (%) | 99.16 | 99.57 | 99.39 | 99.63 | 99.61 | | |
| Solvent: 1.5 times | Selectivity (%) | 99.62 | 99.54 | 99.58 | 99.64 | 99.51 | | |
| (60% $H_2O_2$ was used) | Yield (%) | 98.78 | 99.12 | 98.98 | 99.26 | 99.12 | | |
| [Example 3] | Time after the reaction started (h) | 21 | 39 | 63 | 87 | 118 | 145 | 168 | 192 |
| Temperature: 105° C. | Conversion (%) | 99.01 | 99.43 | 99.29 | 99.43 | 99.42 | 99.37 | 98.18 | 99.26 |
| Solvent: 1.5 times | Selectivity (%) | 9.39 | 99.43 | 99.44 | 99.47 | 99.47 | 99.45 | 99.29 | 99.34 |
| (60% $H_2O_2$ was used) | Yield (%) | 98.41 | 98.87 | 98.74 | 98.90 | 98.89 | 98.82 | 97.49 | 98.61 |
| [Example 4] | Time after the reaction started (h) | 23 | 47 | 71 | 139 | 163 | 195 | 224 |
| Temperature: 115° C. | Conversion (%) | 91.75 | 93.74 | 98.65 | 95.28 | 98.68 | 93.37 | 95.10 |
| Solvent: 1.5 times | Selectivity (%) | 98.86 | 99.04 | 99.29 | 99.07 | 99.10 | 98.09 | 98.76 |
| (60% $H_2O_2$ was used) | Yield (%) | 90.71 | 92.84 | 97.94 | 94.40 | 97.80 | 91.59 | 93.93 |
| [Example 5] | Time after the reaction started (h) | 18 | 42 | 66 | 90 | 114 | 138 | |
| Temperature: 95° C. | Conversion (%) | 99.05 | 99.32 | 99.30 | 99.30 | 99.37 | 99.38 | |
| Solvent: 1.5 times | Selectivity (%) | 99.62 | 99.62 | 99.62 | 99.62 | 99.60 | 99.56 | |
| (45% $H_2O_2$ was used) | Yield (%) | 98.68 | 98.94 | 98.92 | 98.93 | 98.97 | 98.94 | |

What is claimed is:

1. A process for producing a cycloalkanone oxime by conducting a continuous ammoximation reaction in the presence of a titanosilicate catalyst with supplying a cycloalkanone, hydrogen peroxide, ammonia and an organic solvent into the reaction system, wherein the reaction temperature is from 90° C. to 120° C. and the supplying amount of the organic solvent is not more than 2 times by weight of that of the cycloalkanone;

wherein the organic solvent is selected from alcohols having 1 to 6 carbon atoms.

2. A process according to claim 1, wherein the supplying amount of the organic solvent is 0.2 to 1.8 times by weight of that of the cycloalkanone.

3. A process according to claim 1 or 2, wherein the reaction temperature is from 90° C. to 110° C.

4. A process according to claim 1, wherein the supplying amount of the organic solvent is not more than 1.8 times by weight of that of the cycloalkanone.

5. A process according to claim 1, wherein the supplying amount of the organic solvent is not more than 1.5 times by weight of that of the cycloalkanone.

* * * * *